US 6,730,052 B2

(12) United States Patent  
Chow

(10) Patent No.: US 6,730,052 B2  
(45) Date of Patent: May 4, 2004

(54) ELBOW BRACE

(76) Inventor: James C. Y. Chow, 4121 Veterans Memorial Dr., Mount Vernon, IL (US) 62864

( * ) Notice: Subject to any disclaimer, the term of this patent is extended or adjusted under 35 U.S.C. 154(b) by 0 days.

(21) Appl. No.: 09/977,001

(22) Filed: Oct. 12, 2001

(65) Prior Publication Data

US 2003/0073943 A1 Apr. 17, 2003

(51) Int. Cl.$^7$ .................................................. A61F 5/00
(52) U.S. Cl. ............................ 602/20; 602/5; 602/62; 128/881
(58) Field of Search ........................ 602/5, 6, 7, 20, 602/60, 61–63, 4, 26; 128/881, 878, 879; 473/214, 276

(56) References Cited

U.S. PATENT DOCUMENTS

| 3,970,081 | A |   | 7/1976  | Applegate, Jr.          |
|-----------|---|---|---------|-------------------------|
| 4,191,373 | A |   | 3/1980  | Lancellotti             |
| 4,441,493 | A |   | 4/1984  | Nirschl                 |
| 4,479,457 | A | * | 10/1984 | Rotolo ............ 119/850 |
| 4,489,716 | A | * | 12/1984 | Blackwood et al. ... 602/20 |
| 4,504,054 | A | * | 3/1985  | Jackson et al. ....... 473/214 |
| 4,895,142 | A | * | 1/1990  | Liptak ................ 602/4 |
| 4,905,998 | A | * | 3/1990  | Last .................. 602/2 |
| 5,248,292 | A | * | 9/1993  | Holland ............. 602/20 |
| 5,425,539 | A | * | 6/1995  | Steffes ............. 473/214 |
| 5,472,413 | A | * | 12/1995 | Detty ................ 2/16 |
| 5,569,172 | A | * | 10/1996 | Padden et al. ....... 602/20 |
| 5,599,283 | A |   | 2/1997  | Lindenmeyer et al.      |
| 5,628,725 | A | * | 5/1997  | Ostergard ........... 602/20 |
| 5,642,525 | A | * | 7/1997  | Ketola ............... 2/16 |
| 5,891,079 | A |   | 4/1999  | Barnes                  |
| 6,224,564 | B1| * | 5/2001  | Korobow ............. 602/62 |

* cited by examiner

Primary Examiner—Nicholas D. Lucchesi  
Assistant Examiner—Quang D Thanh  
(74) Attorney, Agent, or Firm—Polster, Lieder, Woodruff & Lucchesi, L.C.

(57) ABSTRACT

An elbow brace (10) supporting a person's elbow (E) in a desired, fixed position comprises a sleeve (12) sized to fit over the person's arm (A). One end (14) of the sleeve terminates above the person's elbow, with the other end (16) of the sleeve terminating below the elbow and above the wrist. A support pad (18) fitted into the sleeve pad supports the elbow in the desired position when the sleeve is in place. Straps (24, 26) extend from the one end (14) of the sleeve and about the wearer's neck to secure the sleeve in place.

7 Claims, 2 Drawing Sheets

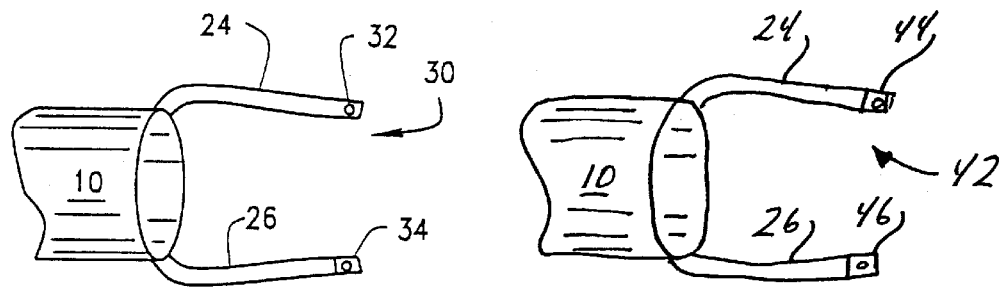
FIG. 4C
FIG. 4E
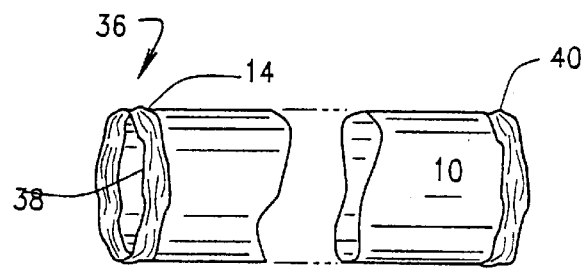
FIG. 4D
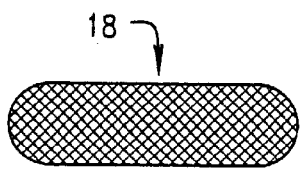
FIG. 5A
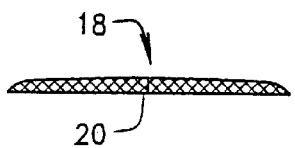
FIG. 5B
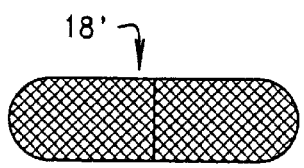
FIG. 6A
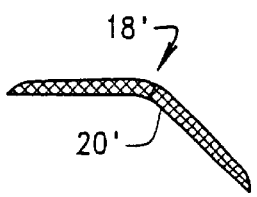
FIG. 6B

ELBOW BRACE

CROSS REFERENCE TO RELATED APPLICATIONS

STATEMENT REGARDING FEDERALLY SPONSORED RESEARCH OR DEVELOPMENT

BACKGROUND OF THE INVENTION

This invention relates to an upper body support; and more particularly, to an elbow brace.

People suffering from elbow injuries such as lateral epiconditis and tardy ulnar nerve syndrome require their elbow to be supported in a fixed position while their condition is being treated. In the former condition, it is important that the elbow be maintained bent; while in the latter condition, it is important that the elbow be kept substantially straight.

Elbow braces are known in the art. See, for example, U.S. Pat. Nos. 5,891,079 and 4,441,493, 4,191,373, and 3,970,081. Since the person requiring use of the support is often engaged in a variety of activities, it is important that any support be relatively lightweight, easy to fit in place and remove, be as unobtrusive as possible, and allow the wearer the freedom to engage in many different activities. Conventional elbow braces have a number of drawbacks. They are cumbersome to put on and uncomfortable to wear. Many braces use materials which chafe against the skin. They employ metal strips that must be adjusted to hold the elbow in the desired position. In this regard, many elbow braces further require belts or straps that have to also be adjusted to hold the strips at appropriate angles to keep the elbow in the proper position when the braces is worn. These metal strips and their associated straps are bulky and make it difficult to wear the brace underneath a shirt or jacket. If the wearer is not careful, parts of the brace can snap and tear their clothing.

BRIEF SUMMARY OF THE INVENTION

In accordance with the present invention, an elbow brace is provided for use by a wearer suffering from a condition requiring the elbow to be immobilized and kept in one position. A sleeve made of a lightweight material is sufficiently long so as to extend from the wearer's wrist to their shoulder. A pair of straps are provided at the one end of the sleeve to allow the brace to be secured about the wearer's neck. A pocket is formed intermediate the length of the sleeve at the location of the elbow. A straight pad or bent pad is fitted into the pocket. The pad is sufficiently rigid so the wearer cannot bend their arm if the straight pad is used, or straighten their arm if the bent pad is used. The pad can be of a molded material contoured to support the elbow. The pad, if heated prior to putting on the brace, will provide a further therapeutic effect to the wearer. The pad can also be a pressure pad applying a constant pressure to the elbow.

The elbow brace is lightweight and can be worn under a shirt or blouse, on the outside of the shirt or blouse, or under a jacket. Importantly, the elbow brace is comfortable to wear while providing the necessary upper body support. The material from which the sleeve is fabricated is flesh colored so as not be readily noticeable. Other objects and features will be in part apparent and in part pointed out hereinafter.

BRIEF DESCRIPTION OF THE SEVERAL VIEWS OF THE DRAWINGS

The objects of the invention are achieved as set forth in the illustrative embodiments shown in the drawings which form a part of the specification.

FIGS. 4A–4E illustrate alternative ways of securing a strap by which the elbow brace is held in place when worn;

FIGS. 5A and 5B are respective plan and elevation views of the pad used with the elbow brace of FIG. 1; and, FIGS. 6A and 6B are similar views of the pad used with the elbow brace of FIG. 2.

Corresponding reference characters indicate corresponding parts throughout the several views of the drawings.

DETAILED DESCRIPTION OF INVENTION

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. As various changes could be made in the above constructions without departing from the scope of the invention, it is intended that all matter contained in the above description or shown in the accompanying drawings shall be interpreted as illustrative and not in a limiting sense.

Figure 1:
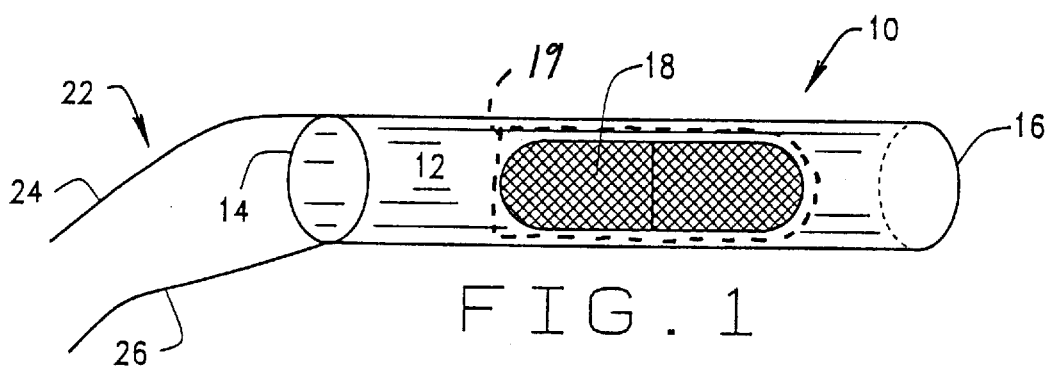
FIG. 1 is a perspective view of an elbow brace comprising a first embodiment of the invention.
Figure 2:
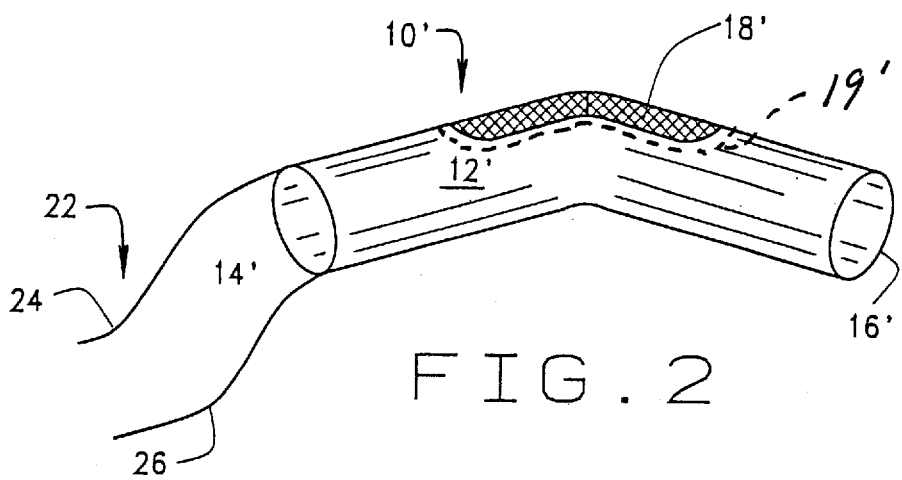
FIG. 2 is a perspective view of an elbow brace comprising a second embodiment of the invention.
Figure 3:
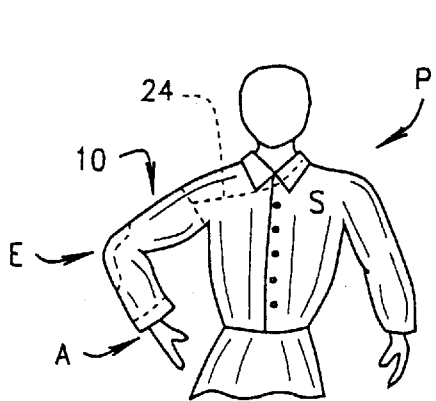
FIG. 3 is a simplified illustration showing wearing of an elbow brace of the present invention under a person's clothing.

Referring to the drawings, an elbow brace for supporting a person's (P) elbow (E) in a desired, fixed position is indicated generally 10 in FIG. 1, and 10' in FIG. 2. The brace first includes a sleeve (12) sized to fit over the person's arm (A) with one end (14) of the sleeve terminating above the person's elbow and the other end (16) of the sleeve terminating below the elbow, preferably somewhere above the wrist. As shown in FIG. 3, the length of sleeve 12 is such that it can be comfortably worn beneath a shirt S or a jacket and not be discernible to others. The sleeve is available in different diameters and lengths so to fit over the arm of a wide range of wearers. Those skilled in the art will appreciate that a person's upper arm is typically bigger than their lower arm. Accordingly, sleeve 10 or 10' may be made such that the diameter of the sleeve at end 14 is bigger than the sleeve diameter at end 16. The sleeve is fabricated of a thin, lightweight, washable cotton or polyester material. The sleeve can also be made of a flesh colored material so as to not be readily noticeable by others. When in place, the sleeve material will not fold or gather so support pad 18 or 18' does not slip out of place.

The support pad 18 or 18' carried by the sleeve supports the elbow in a fixed straight or bent position, as appropriate. As shown in FIGS. 5A and 5B, an elongate, generally straight pad 18 is for use in brace 10 when the arm and elbow are kept straight. In FIGS. 6A and 6B, an elongate, generally L-shaped pad 18' is for use in brace 10' when the arm is to be kept bent. Pad 18 or 18' is either sewn into sleeve 12 or 12'; or, the sleeve includes a pocket 19 or 19' in which the pad is inserted. This latter construction has the advantage of allowing the pad to be removed for washing or replacement. The pad also has an inner surface 20 or 20' contoured to the shape of the elbow. Surface 20 of pad 18 is contoured for the shape of the elbow when the arm is kept straight; while surface 20' of pad 18' is contoured to the shape of the elbow when the arm is bent.

The pad can be made of a heat absorbent material. In this application, the pad is heated to a predetermined temperature before the brace is put on. The pad then heats the elbow during the time the brace is being worn. The pad can also be made of an inflatable material. Now, when the brace is worn, the pad is inflated so pressure is constantly applied to the elbow. In either instance, an additional therapeutic value is achieved besides keeping the elbow immobilized.

Figure 4A:
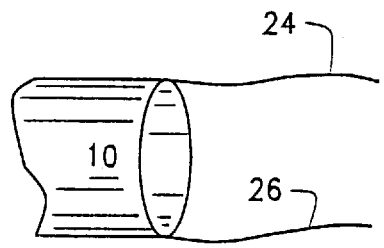
Figure 4B:
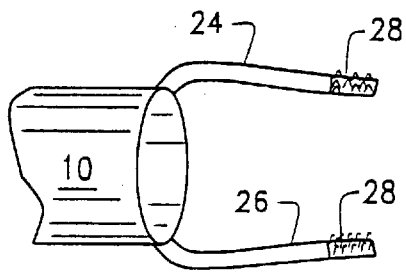

Elbow brace 10 or 10' further includes a securing means 22 at least one end of sleeve 12 or 12' for holding the sleeve in place while being worn. This maintains pad 18 or 18' in a desired position supporting the elbow. In FIGS. 1 and 2, a preferred embodiment of means 22 is implemented using straps 24, 26 extending from ends 14, 14' of sleeves 12, 12'. As shown in FIG. 3, the straps are sufficiently long so to extend about the wearer's neck. The straps can be used to secure the sleeve in place in a number of ways. In the embodiment of FIG. 4A, for example, the distal end of the respective straps are simply tied together. In the embodiment of FIG. 4B, segments 28 of a velcro-type material are attached to respective distal end of each strap. The segments are then brought together and attach to each other. In the embodiment of FIG. 4C, a hook and eyelet arrangement 30 is employed with the hook 32 being fitted onto the distal end of strap 24 and the eyelet 34 onto the distal end of strap 26. The hook is inserted through the eyelet to hold the brace in place. Similarly, a snap fastener, not shown, is mounted to the respective distal ends of the straps to secure the straps about the wearer's neck. Those skilled in the art will recognize that other means of securing besides these can also be employed.

Referring to FIG. 4D, an alternative securing means 36 includes an elasticized cuff 38 attached to the end 14 of sleeve 10. The cuff binds the upper end of the sleeve sufficiently tightly about the upper arm of the wearer that the sleeve will not be displaced. In addition, another elasticized cuff 40 is attached to end 16 of the sleeve.

In FIG. 4E, another sleeve securing means 42 includes a snap fastener 44, 46, the components of which are at the ends of the respective straps 24, 26.

In view of the above, it will be seen that the several objects and advantages of the present invention have been achieved and other advantageous results have been obtained. In particular, an upper body support is provided to hold an elbow is a straight or bent condition, as appropriate. By immobilizing the elbow, and by the capability of applying heat and/or pressure to the area about the elbow, conditions such as lateral epiconditis and tardy ulnar nerve syndrome can be effectively treated.

Having thus described the invention, what is claimed and desired to be secured by Letters Patent is:

1. An elbow brace for supporting a person's elbow in a desired, fixed position comprising:

a sleeve fitting over the person's arm with one end of the sleeve terminating above the person's elbow and the other end of the sleeve terminating below the elbow;

a pocket formed in the sleeve and extending from above the elbow to below the elbow;

a single pad enclosed within the pocket so to be carried by the sleeve, the pad supporting the elbow in the fixed position when the sleeve is in place and being of unitary construction, the pad comprising an elongate, generally straight pad having in inner surface of which is contoured to the shape of the elbow when the arm is straight so to keep the elbow in a straightened position when the sleeve is in place; and, a pair of straps extending from said one end of the sleeve, the straps being sufficiently long so to extend about the person's to secure the sleeve in place.

2. The elbow brace of claim 1 in which the sleeve is such that the upper end of the sleeve terminates below the shoulder and the lower end of the sleeve terminates above the wrist.

3. The elbow brace of claim 1 in which hook and loop fasteners are attached to distal ends of each strap to secure the straps about the person's neck.

4. The elbow brace of claim 1 in which a hook and eyelet fastener is mounted to respective distal ends of the straps to secure the straps about the person's neck.

5. The elbow brace of claim 1 in which a snap fastener is mounted to the respective distal ends of the straps to secure the straps about the person's neck.

6. The elbow brace of claim 1 wherein the pad comprises a heated pad so to apply heat to the person's elbow when the brace is worn.

7. The elbow brace of claim 1 wherein the pad is a pressure pad that exerts pressure on the elbow when the brace is worn.

* * * * *

UNITED STATES PATENT AND TRADEMARK OFFICE
CERTIFICATE OF CORRECTION

PATENT NO. : 6,730,052 B2
DATED : May 4, 2004
INVENTOR(S) : James C.Y. Chow

It is certified that error appears in the above-identified patent and that said Letters Patent is hereby corrected as shown below:

<u>Column 4,</u>
Line 18, after the word "having" and before the word "inner", replace "in" with -- an --.
Line 25, after the word "persons" and before the word "to", insert -- neck --.
Line 26, after the word "the", and before the word "sleeve", insert the phrase -- length of the --.
Line 30, after the word "which", replace "hook and loop" with -- velcro-type --.

Signed and Sealed this

Thirteenth Day of December, 2005

JON W. DUDAS
*Director of the United States Patent and Trademark Office*